United States Patent [19]

Taylor et al.

[11] Patent Number: 5,243,052
[45] Date of Patent: Sep. 7, 1993

US005243052A

[54] MIXED CARBONATE ESTER DERIVATIVES OF QUINOPHTHALONE DYES AND THIER PREPARATION

[75] Inventors: Lloyd D. Taylor; David P. Waller, both of Lexington, Mass.

[73] Assignee: Polaroid Corporation, Cambridge, Mass.

[21] Appl. No.: 548,223

[22] Filed: Jun. 29, 1990

[51] Int. Cl.$^5$ .................. C09B 25/00; C07D 405/04; C07D 215/14

[52] U.S. Cl. .................................. 546/154; 546/167; 546/173

[58] Field of Search .................. 546/167, 154, 173

[56] References Cited

U.S. PATENT DOCUMENTS

| | | | |
|---|---|---|---|
| 3,488,705 | 6/1970 | Fox et al. ................. | 96/1.6 |
| 3,723,121 | 3/1973 | Hauser et al. ............. | 96/27 |
| 3,745,009 | 7/1974 | Jenkins et al. ............ | 96/84 R |
| 3,832,212 | 8/1974 | Jenkins et al. ............ | 117/36.7 |
| 4,242,440 | 12/1980 | Yee et al. ................ | 430/346 |
| 4,380,629 | 4/1983 | Yamashita et al. ......... | 542/455 |
| 4,602,263 | 7/1986 | Borrer et al. ............. | 346/201 |
| 4,663,518 | 5/1987 | Borrer et al. ............. | 235/487 |
| 4,720,449 | 1/1988 | Borrer et al. ............. | 430/338 |
| 4,826,976 | 5/1989 | Borrer et al. ............. | 544/58.4 |

FOREIGN PATENT DOCUMENTS 63-182192 7/1988 Japan .

OTHER PUBLICATIONS

Chemical Abstracts, 110, 85,692q (Abstract of Japanese Patent Application 87-13,648, Publication No. 63-182,192, published Jul. 27, 1988).

Chemical Abstracts, 111, 123,964k (Abstract of Japanese Patent Application 87-243,331, Publication No. 01-85,792, published Mar. 30, 1989).

Chemical Abstracts, 112(3), 22540j (Abstract of Japanese Patent Application 87-296,452, Publication No. 01-136,787, published May 30, 1989).

Greene, Theodora W., Protective Groups in Organic Synthesis, New York, Wiley, 1981, p. 326.

Kosar, J. Light-Sensitive Systems: Chemistry and Applications of Nonsilver Halide Photographic Processes, New York, Wiley, 1965, pp. 402-419.

Manukian, B. K., and Mangini, A., Chinophthalone, Chimia, 24, 328-339 (197).

Zollinger, Heinrich, Color Chemistry, VCH, pp. 52-53 (1971).

Primary Examiner—David B. Springer
Attorney, Agent, or Firm—David J. Cole

[57] ABSTRACT

A mixed carbonate ester of a quinophthalone dye and a tertiary alkanol containing not more than about 9 carbon atoms, preferably a compound of the formula:

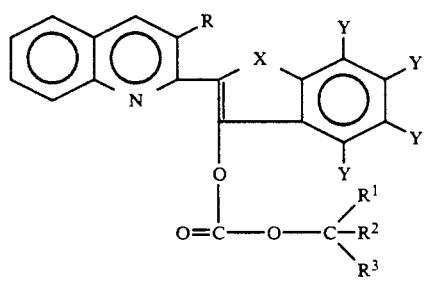

wherein X is a sulfur atom or a carbonyl group; each Y independently is a hydrogen atom, a halogen atom, a $-CO-OR^4$ or a $-CO-NHR^4$ group, wherein $R^4$ is an alkyl group containing not more than about 10 carbon atoms; R is a hydrogen atom or an $-O-C(=O)-O-CR^5R^6R^7$ group; and $R^1$, $R^2$, $R^3$, $R^5$, $R^6$ and $R^7$ are each an alkyl group, subject to the proviso that $R^1$, $R^2$ and $R^3$ together contain a total of not more than about 8 carbon atoms, and $R^5$, $R^6$ and $R^7$ together contain a total of not more than about 8 carbon atoms.

16 Claims, 4 Drawing Sheets

MIXED CARBONATE ESTER DERIVATIVES OF QUINOPHTHALONE DYES AND THIER PREPARATION

BACKGROUND OF THE INVENTION

This invention relates to methods and materials for thermal imaging. More specifically, this invention relates to certain mixed carbonate esters of quinophthalone dyes, to the use of these mixed esters in thermal imaging, and to heat-sensitive elements containing these mixed esters.

A variety of thermal imaging systems for producing color images have been proposed, and several have been mentioned in Kosar, J., Light-Sensitive Systems: Chemistry and Application of Nonsilver Halide Photographic Processes, New York, John Wiley and Sons, Inc., 1965, pp. 402-19. In one type of heat-sensitive recording system, a first sheet containing a first reagent is superposed over a second sheet containing a second reagent and one of the reagents is melted or vaporized by the imagewise application of heat and transferred for reaction with the other reagent to form a color image. In another type of dye transfer system, images are formed by sequentially transferring two or more dyes carried on separate donor sheets to a common receptor sheet by melting or volatilization. In thermal imaging systems of the "self-containing" type, a single sheet is used and the imagewise heating of the heat-sensitive sheet produces a color image, for example, by rendering a coating layer transparent to reveal the color of a background layer, by initiating the chemical reaction of two or more reagents to form a colored product or by bleaching, coloring or changing the color of a single reagent. In most of the non-silver thermal imaging systems in commercial use, color images are formed using two or more reagents that usually are encapsulated or otherwise isolated from each other until melted and mixed upon imagewise heating.

A number of compounds which undergo a color change from a colorless to a colored form, from one color to another color or from a colored to a colorless form upon application of heat have been disclosed. For example, U.S. Pat. No. 3,723,121, issued Mar. 27, 1973, discloses several thermochromic materials for laser beam recording including inorganic compounds, such as black copper (II) oxide which decomposes to red copper (I) oxide upon heating, and organic compounds, such as polyacetylene compounds which subsequent to treatment with ultraviolet light undergo two changes in color, first to red then to yellow, as the temperature is increased. U.S. Pat. No. 4,242,440, issued Dec. 30, 1980, discloses another class of heat-sensitive polyacetylene compounds which exhibit color changes, for example, gold to red, brown to orange and gold to orange, which color changes are reversible. U.S. Pat. No. 3,488,705, issued Jun. 1, 1970, discloses thermally unstable organic acid salts of triarylmethane dyes useful in electrophotographic elements as sensitizing dyes that are decomposed and bleached upon heating. U.S. Pat. No. 3,745,009, originally issued Jul. 10, 1974 and reissued as Reissue No. 29,168, and U.S. Pat. No. 3,832, 212, issued Aug. 27, 1974, disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO— radical and a dye base or dye radical, which may in part fragment further. U.S. Pat. No. 4,380,629, issued Apr. 19, 1983, discloses styryl-like compounds which undergo coloration or bleaching, reversibly or irreversibly via ring-opening and ring-closing in response to activating energies such as light, heat, electric potential and so on.

U.S. Pat. No. 4,720,449, issued Jan. 19, 1988, describes a thermal imaging method which comprises heating imagewise a di- or triarylmethane compound possessing within its di- or triarylmethane structure an aryl group substituted in the ortho position to the meso carbon atom with a moiety ring-closed on the meso carbon atom directly through a nitrogen atom, which nitrogen atom is also bound to a group with a masked acyl substituent that undergoes fragmentation upon heating to liberate the acyl group for effecting intramolecular acylation of the nitrogen atom to form a new group in the ortho position, whereby the di- or triarylmethane compound is rendered colored in an imagewise pattern corresponding to the imagewise heating.

U.S. Pat. No. 4,663,518, issued May 5, 1987, describes an identification card comprising a single medium having a plurality of different heat sensitive image forming dye compounds on which are encoded a colored pictorial image of the card holder, colored text, and machine readable digital data. A laser printing method is provided for activating the heat sensitive image forming dyes to provide the colored pictorial image of the card holder, colored text, and machine readable digital data.

U.S. Pat. No. 4,602,263, issued Jul. 22, 1986, and U.S. Pat. No. 4,826,976, issued May 2, 1989, both describe thermal imaging systems for optical recording and particularly for forming color images. This thermal imaging method relies upon the irreversible unimolecular fragmentation of one or more thermally unstable carbamate moieties of an organic compound to effect a visually discernible color shift from colorless to colored, from colored to colorless or from one color to another. These patents also describe an imaging dye of the formula:

$$[M(X)_q]_pD$$

wherein M is a carbamate moiety: X is —N=, —SO$_2$—, or —CH$_2$—; D taken with X and M represents the residue of an organic dye; q is 0 or 1; and p is a whole number of at least 1 and usually is a whole number of 1 to 3. Preferably, M has the formula:

wherein R is alkyl usually having 1 to 4 carbon atoms; —SO$_2$R$_1$ wherein R$_1$ is alkyl usually having 1 to 6 carbon atoms; phenyl; naphthyl; or phenyl substituted with alkyl usually having 1 to 6 carbon atoms, alkoxy usually having 1 to 6 carbon atoms, halo, such as chloro or bromo, trihalomethyl, such as trichloromethyl or trifluoromethyl, cyano, nitro, carboxy, —CONR$_2$R$_3$ wherein R$_2$ and R$_3$ each are hydrogen or alkyl usually having 1 to 6 carbon atoms, —CO$_2$R$_4$ wherein R$_4$ is alkyl usually having 1 to 6 carbon atoms or phenyl, —COR$_5$ wherein R$_5$ is amino, alkyl usually having 1 to 6 carbon atoms or phenyl, —NR$_6$R$_7$ wherein R$_6$ and R$_7$ each are hydrogen or alkyl usually having 1 to 6 carbon atoms, —SO$_2$—NR$_8$R$_9$ wherein R$_8$ and R$_9$ each are hydrogen, alkyl usually having 1 to 6 carbon atoms or benzyl; and Z is an acyloxy group, —COOR$_{10}$, wherein R$_{10}$ is a tert-alkyl or —(CH$_2$)$_2$Y group, wherein Y is an electron-withdrawing group. It is stated in column 4 of each patent that D may be the residue of:

a triarylmethane dye, a xanthene dye, a rhodamine dye, a fluoran dye, an azocarbocyanine dye, a benzylidine dye, a thiazine dye, an acridine dye, an aminoanthraquinone dye or other dye containing a nitrogen atom possessing a lone pair of electrons, which when substituted with said acyloxy group to form said carbamate moiety, will be color-shifted. Preferably a tert-alkoxy carbonyl group, such as, tert-butoxycarbonyl is used as the acyloxy group to isolate the lone pair of electrons on the nitrogen atom of the organic dye to effect said color shifting. The fragmentation of the resulting carbamate moiety upon application of heat releases said lone pair of electrons to effect a visually discernible change in the spectral absorption characteristics of the dye, preferably, from colored to colorless or colorless to colored.

The use of tert-butoxycarbonyl (hereinafter "t-BOC") as a protecting group for nitrogen functionalities is well known, and the thermal lability, i.e., instability of this protecting group at 150°-170° C. is mentioned in Greene, Theodora W., Protective Groups in Organic Synthesis, New York, John Wiley and Sons, Inc., 1981, page 326.

Despite the development of all the prior art dyes discussed above, there are still difficulties in producing a satisfactory yellow image in a multi-color thermal imaging system. Many proposed dyes undergo a change from yellow to colorless on exposure to heat, whereas for imaging purposes it is preferred that the color change be from colorless to colored. Many yellow thermal imaging leuco dyes (the term "leuco dye" is used herein to refer to a substantially colorless compound which generates a colored material upon heating) undergo slow thermal breakdown at room temperature, thus restricting the shelf life of imaging materials containing the leuco dye, especially in warm climates. Furthermore, it is difficult to produce a yellow thermal imaging dye in which the absorption shift between the leuco dye and the dye is so large that the leuco dye is essentially colorless, while the yellow dye provides high extinction in the yellow region, and is sufficiently stable that the resultant image does not fade upon extended storage; many proposed yellow leuco dyes have a pale yellow color, which undesirably affects the background color of any image produced.

Accordingly, there is still a need for a yellow thermal imaging leuco dye which is stable for long periods at room temperature, which is substantially colorless so that it does not affect the background color of an image. This invention provides leuco dyes, and methods and materials for thermal imaging which meet these requirements and which produce high quality yellow images. Related compounds of the invention also make good orange to red dyes which may be used to produce high quality images.

SUMMARY OF THE INVENTION

This invention provides a mixed carbonate ester of a quinophthalone dye and a tertiary alkanol containing not more than about 9 carbon atoms. This mixed ester is preferably of the of the formula:

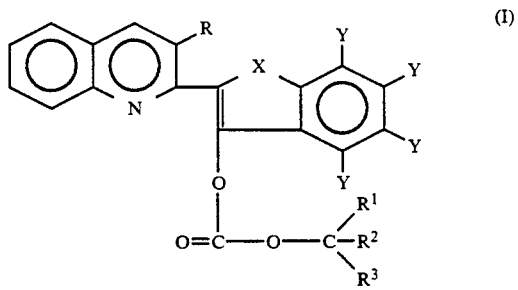

wherein X is a sulfur atom or a carbonyl group; each Y independently is a hydrogen atom, a halogen atom, a —CO—OR$^4$ or a —CO—NHR$^4$ group, where R$^4$ is an alkyl group containing not more than about 10 carbon atoms; R is a hydrogen atom or an —O—C(=O)—O—CR$^5$R$^6$R$^7$ group; and R$^1$, R$^2$, R$^3$, R$^5$, R$^6$ and R$^7$ are each an alkyl group, subject to the proviso that R$^1$R$^2$ and R$^3$ together contain a total of not ore than about 8 carbon atoms, and R$^5$, R$^6$ and R$^7$ together contain a total of not more than about 8 carbon atoms.

This invention also provides a heat-sensitive element comprising a support carrying at least one imaging layer of one of the aforementioned mixed carbonate esters.

This invention also provides a method of thermal imaging which comprises heating imagewise a heat-sensitive element comprising a support carrying at least one imaging layer of one of the afornenetioned mixed carbonate esters, thereby causing, in the heated areas, breakdown of at least one carbonate ester grouping in the mixed ester, whereby the compound is rendered colored in an imagewise pattern corresponding to the imagewise heating.

This invention also provides a process for the preparation of the aforementioned mixed esters, which process reacting the corresponding free quinophthalone dye with the corresponding di-alkanol dicarbonate in the presence of a base. In the case of the preferred compounds of Formula I above, this process comprises reacting the corresponding compound of the formula:

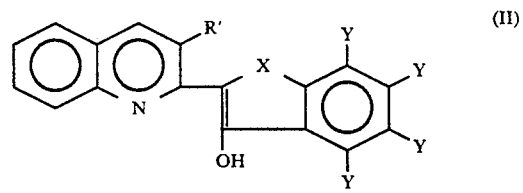

wherein R' is a hydrogen atom or a hydroxyl group; each Y independently is a hydrogen atom, a halogen atom, a —CO—OR$^4$ or a —CO—NHR$^4$ group, where R$^4$ is an alkyl group containing not more than about 10 carbon atoms; and X is a sulfur atom or a carbonyl group, with the corresponding di-tertiary alkyl dicarbonate in the presence of a base.

DETAILED DESCRIPTION OF THE INVENTION

Figure 1:
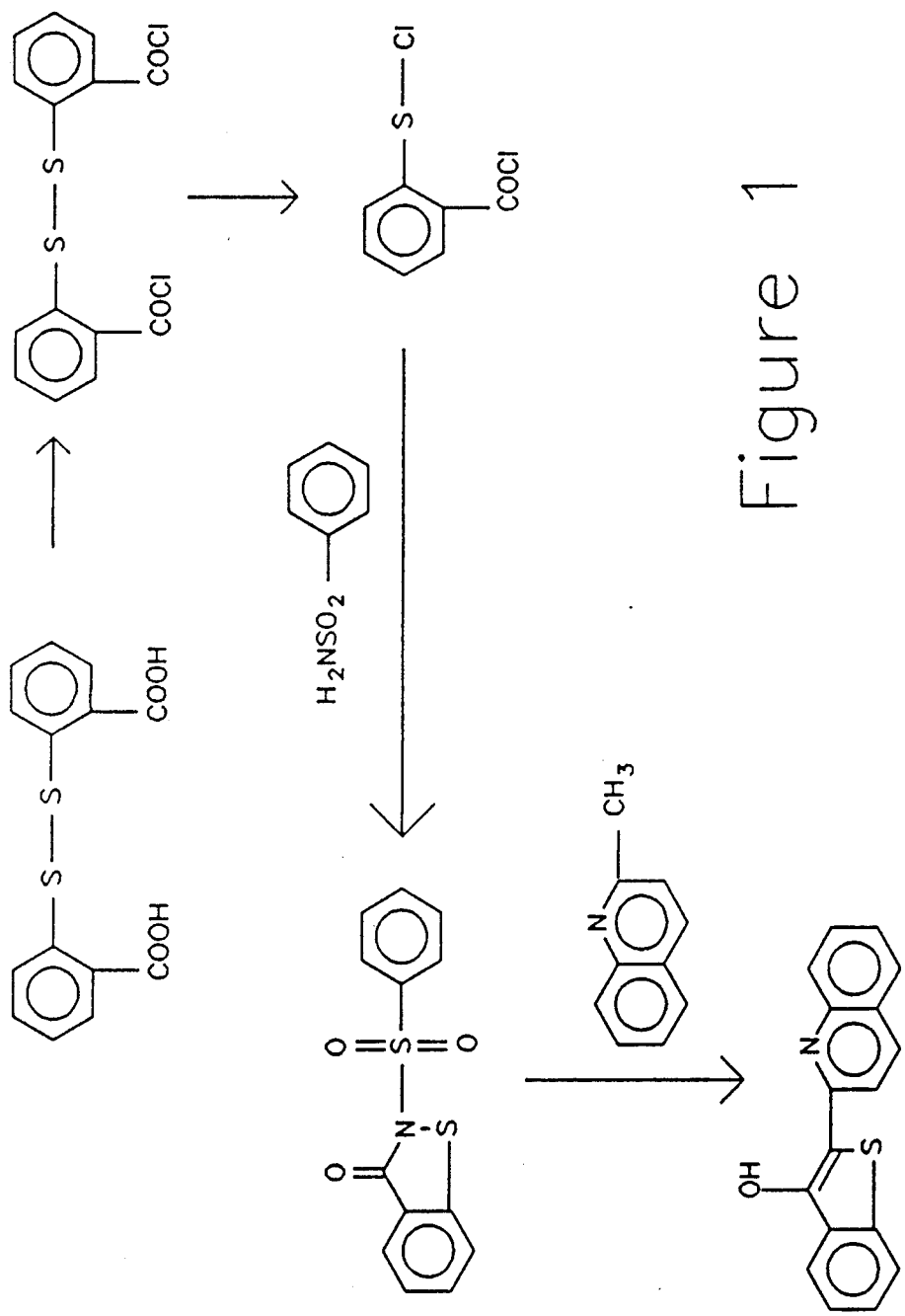
FIG. 1 of the accompanying drawings shows a synthetic route to a compound of the present invention in which X is a sulfur atom, as described in Example 3 below.

The preferred mixed esters of the invention are those in which the tertiary alkanol contains not more than about 6 carbon atoms. Thus, in the preferred esters of Formula I, desirably $R^1$, $R^2$ and $R^3$ together contain not more than about 5 carbon atoms; preferably, $R^1$, $R^2$ and $R^3$ are each methyl groups. Similarly, in the preferred esters of Formula I in which R is an —O—C(=O)—O—CR$^5$R$^6$R$^7$ group, desirably $R^5$, $R^6$ and $R^7$ together contain not more than about 5 carbon atoms; preferably, $R^5$, $R^6$ and $R^7$ are each methyl groups. Also, X is preferably a carbonyl group, and each Y is preferably a hydrogen atom.

Two preferred quinophthalone dyes for use in the present invention are quinoline yellow and terasil yellow. Specific preferred esters of these dyes are the t-BOC derivative of quinoline yellow (the compound of Formula I in which R is a hydrogen atom; X is a carbonyl group; each Y is a hydrogen atom; and $R^1$, $R^2$ and $R^3$ are each a methyl group) and the bis(t-BOC) derivative of terasil yellow (the compound of Formula I in which R is an —O—C(=O)—O—C(CH$_3$)$_3$ group; X is a carbonyl group; each Y is a hydrogen atom; and $R^1$, $R^2$ and $R^3$ are each a methyl group).

The heat-sensitive mixed esters of the present invention may be used to produce color images of pictorial quality for color hard copy. Upon exposure to temperatures of about 150°-200° C., these esters undergo a unimolecular fragmentation, with elimination of carbon dioxide and an alkene, to give the free quinophthalone dye; this liberation of the free dye causes a change in the spectral absorption peak from the ultraviolet to the visible region of the spectrum, and can be achieved rapidly and efficiently and without the problems associated with isolating and then bringing two reagents together to effect image formation, as in some prior art thermal imaging systems. Because the formation of the free quinophthalone dye is irreversible, changes in image density, e.g., in the highlight areas due to a reversal in bleaching or in the saturated areas due to a reversal in coloration, are obviated. Also, the liberation of the free dye can be achieved at moderately elevated temperatures above ambient temperatures so that the heat required for effecting the fragmentation can be kept below levels that would cause deformation or distortion of the imaging layer or other layers of a heat-sensitive element. Since image formation does not involve transfer and registration of separate colors, multi-color images of excellent sharpness and resolution can be readily obtained by using the mixed esters of the present invention in imaging media containing additional dyes of other colors.

The preferred mixed esters of the invention in which X is a carbonyl group upon generally liberate yellow dyes, while the mixed esters in which X is a sulfur atom upon heating generally liberate orange to red dyes. Both groups of mixed esters are essentially colorless.

Some mixed esters of the present invention, such as those of Formula I in which R is an —O—C(=O)—O—CR$^4$R$^5$R$^6$ group, contain two labile ester groupings, and obviously during thermal imaging with such a diester one ester grouping may break down before the other. However, it has been found that the breakdown of one ester grouping produces a compound having a color very similar to that of the free quinophthalone dye itself, so that the presence of monoester in an imaging medium does not interfere with the formation of the desired image. Specifically, it has been found that the ester grouping on the five-membered ring is the more labile, and therefore the resultant monoester, which in the case of a terasil yellow derivative may be, for example of the formula:

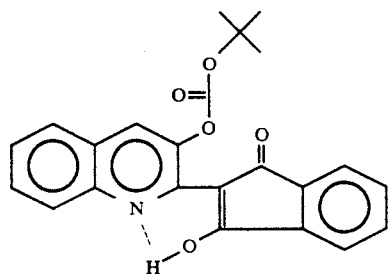

is a substituted quinoline yellow dye and thus does not interfere with the desired yellow image.

As already mentioned, the mixed esters of the present invention may be prepared by reacting the corresponding free quinophthalone dye with the corresponding di-alkanol dicarbonate in the presence of a base. The ready formation of the mixed esters of the present invention by this process is surprising, since the quinophthalone dyes will not undergo acylation or similar reactions under the same conditions. The present inventors have attempted to react quinoline yellow with acetic anhydride under the preferred conditions for preparation of the corresponding t-BOC derivative (see Example 1 below), but failed to prepare any of the acyl derivative.

Quinophthalone dyes, including the compounds of Formula II in which X is a carbonyl group, are well-known and processes for their preparation are described in the literature. Indeed, quinoline yellow and terasil yellow are available commercially. The corresponding thiocompounds, such as the compounds of Formula II in which X is a sulfur atom, may be prepared by the synthetic route shown in FIG. 1, which illustrates the preparation of the thio-analogue of quinoline yellow and its conversion to the corresponding leuco dye of Formula I.

As shown in FIG. 1, 2,2'-dithiobenzoic acid (III) is treated with thionyl chloride to produce the corresponding diacid chloride (IV), the disulfide linkage of which is broken with chlorine to produce m-chlorosulfylbenzoyl chloride (V). This benzoyl chloride is condensed with benzenesulfonamide in the presence of pyridine to produce benzenesulfonylbenzisothiazolone (VI), which is treated with quinaldine to produce the desired dye (VII). This dye (VII) may then be converted to its t-BOC derivative as described above.

In carrying out the thermal imaging method of the present invention, heat may be applied or induced imagewise in a variety of ways, for example, by direct application of heat using a thermal printing head or thermal recording pen or by conduction from heated image-markings of an original using conventional thermographic copying techniques. Preferably, selective heating is produced in the heat-sensitive element itself by the conversion of electromagnetic radiation into heat, and preferably the light source is a laser beam emitting source such as a gas laser or semiconductor laser diode. The use of a laser beam is not only well suited for recording in a scanning mode but by utilizing a highly concentrated beam, radiant energy can be concentrated in a small area so that it is possible to record at high speed and high density. Also, it is a convenient way to record data as a heat pattern in response to transmitted signals, such as digitized information, and a convenient way of preparing multicolor images by employing a plurality of laser beam source that emit laser beams of different wavelengths.

Since the leuco dyes of the present invention absorb strongly in the ultraviolet, in theory imaging could be effected using an ultraviolet laser. However, at present ultraviolet lasers are not well-suited to imaging processes, and such processes are preferably carried out using an infra-red laser. Accordingly, in a preferred embodiment, the heat-sensitive element contains an infra-red absorbing substance for converting infra-red radiation into heat, which is transferred to the heat-sensitive compound to initiate the fragmentation reaction and effect the change in the absorption characteristics of the heat-sensitive compounds from colorless to colored. Obviously, the infra-red absorber should be in heat-conductive relationship with the heat-sensitive compound, for example, in the same layer as the heat-sensitive compound or in an adjacent layer. Though an inorganic compound may be employed, the infra-red absorber preferably is an organic compound, such as a cyanine, merocyanine, squarylium or thiopyrylium dye, and preferably, is substantially non-absorbing in the visible region of the electromagnetic spectrum so that it will not contribute any substantial amount of color to the $D_{min}$ areas, i.e., the highlight areas of the image. The light absorbed by the respective heat-sensitive compounds is converted into heat and the heat initiates the irreversible fragmentation reaction to effect the formation of colored compounds.

The thermal decomposition of the leuco dyes of the present invention is subject to general acid/base catalysis. Accordingly, attention should be paid to the degree of acidity or basicity of any medium in which the leuco dyes are to be distributed. Typically, the present heat-sensitive element will comprise the leuco dye in a polymer, and any pendant acidic or basic groups on the polymer may affect the rate of thermal decomposition of the leuco dye, and thus the sensitivity of the heat-sensitive element.

In a multi-color imaging system, the mixed esters of the present invention are used to form the yellow or red image, while any of the known imaging dyes may be used to form the other colored images. Typically, the heat-sensitive element used in such a multi-color imaging system will contain, in addition to any yellow imaging layer of the mixed esters of the present invention, an imaging layer of colorless imaging compound for forming a cyan image, and an imaging layer of colorless imaging compound for forming a magenta image. Any known cyan and magenta leuco dyes may be used in the appropriate layer; a preferred cyan leuco dye is that of the formula:

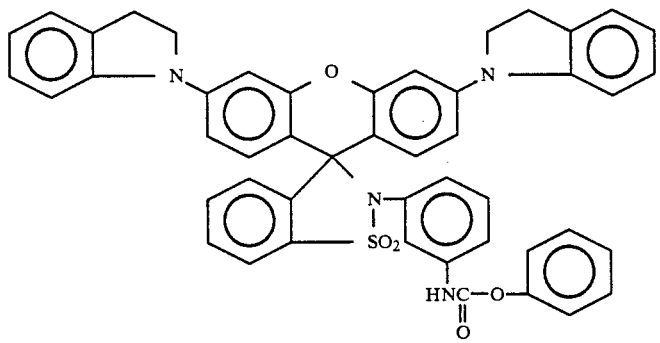

while a preferred magenta leuco dye is that of the formula:

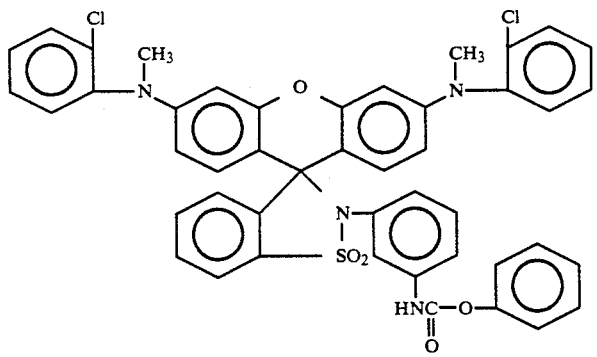

These preferred cyan and magenta leuco dyes, and processes for their preparation, are described in the aforementioned U.S. Pat. No. 4,664,518.

In the production of such multi-color images, the leuco dyes are desirably selected such that they absorb radiation at different predetermined wavelengths above 700 nm sufficiently separated so that each imaging layer may be exposed separately and independently of the others by using infra-red radiation at the particular wavelengths selectively absorbed by the respective infra-red absorbers. As an illustration, the imaging layer containing the mixed ester of the present invention, and the magenta and cyan precursors may have infra-red absorbers associated therewith that absorb radiation at 760 nm, 820 nm and 880 nm, respectively, and may be addressed by laser beam sources, for example, infra-red laser diodes emitting laser beams at these respective wavelengths so that the three imaging layers can be exposed independently of one another. While each layer may be exposed in a separate scan, it is usually preferred to expose all of the imaging layers simultaneously in a single scan using multiple laser beam sources of the appropriate wavelengths. Instead of using superimposed imaging layers, the heat-sensitive compounds and associated infra-red absorbers may be arranged in an array of side-by-side dots or stripes in a single recording layer.

In a further embodiment, multicolor images may be produced using the same infra-red absorbing compound in association with each of two or more superposed imaging layers and exposing each imaging layer by controlling the depth of focussing of the laser beam. In this embodiment, the concentration of infra-red absorber is adjusted so that each of the infra-red absorbing layers absorb approximately the same amount of laser beam energy. For example, where there are three infra-red absorbing layers, each layer would absorb about one-third of the laser beam energy. It will be appreciated that controlling the focussing depth to address each layer separately may be carried out in combination with the previous embodiment of using infra-red absorbers that selectively absorb at different wavelengths in which instance the concentration of infra-red absorber would not have to be adjusted for the laser beam energy since the first infra-red dye would not absorb any substantial amount of radiation at the absorption peaks of the second and third dyes and so forth.

Where imagewise heating is induced by converting light to heat as in the embodiments described above, the heat-sensitive element may be heated prior to or during imagewise heating. This may be achieved using a heating platen or heated drum or by employing an additional laser beam source or other appropriate means for heating the element while it is being exposed imagewise.

In addition to the imaging layer containing the mixed ester and any other imaging layers containing other heat-materials, the heat-sensitive elements of the present invention may comprise additional layers, for example, a subbing layer to improve adhesion to the support, interlayers for thermally insulating the imaging layers from each other, an anti-abrasive topcoat layer (which also may function as a UV protecting layer by including an ultraviolet absorber therein) or other auxiliary layers. The heat-sensitive compounds are selected to give the desired color or combination of colors, and for multicolor images, the compounds selected may comprise the subtractive primaries yellow, magenta and cyan or other combinations of colors, which combinations may additionally include black. As noted previously, the compounds generally are selected to give the subtractive colors cyan, magenta and yellow, as commonly employed in photographic processes to provide full natural color.

The support employed may be transparent or opaque and may be any material that retains its dimensional stability at the temperature used for image formation. Suitable supports include paper, paper coated with a resin or pigment, such as calcium carbonate or calcined clay, synthetic papers or plastic films, such as polyethylene, polypropylene, polycarbonate, cellulose acetate, polyethylene terephthalate and polystyrene.

Usually the or each layer containing heat-sensitive compound contains a binder and is formed by combining the heat-sensitive compound and the binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking where thermal recording heads or thermal pens are used to apply the imagewise pattern of heat. In forming the layer(s) containing the heat-sensitive compounds and the interlayers or other layers, temperatures should be maintained below levels that will initiate the fragmentation reaction so that the heat-sensitive compounds will not be prematurely colored or bleached.

Examples of binders that may be used include polyvinyl alcohol, polyvinyl pyrrolidone, methyl cellulose, cellulose acetate butyrate, copolymers of styrene and butadiene, polymethyl methacrylate, copolymers of methyl and ethyl acrylate, polyvinyl acetate, polyvinyl butyral, polycarbonate and polyvinyl chloride. A preferred binder is polyethyl oxazoline. It will be appreciated that the binder selected should not have any adverse effect on the heat-sensitive compound incorporated therein and may be selected to have a beneficial effect. Also, the binder should be heat-stable at the temperatures encountered during image formation and it should be transparent so that it does not interfere with viewing of the color image. Where electromagnetic radiation is employed to induce imagewise heating, the binder also should transmit the light intended to initiate image formation.

The following Examples are now given, though by way of illustration only, to show details of particularly preferred reagents, conditions and techniques used in the compositions and methods of the present invention.

Example 1: Preparation of t-BOC derivative of quinoline yellow

This Example illustrates the preparation of the t-BOC derivative of quinoline yellow, the compound of Formula I in which R and $R^4$ are each a hydrogen atom; X is a carbonyl group; and $R^1$, $R^2$ and $R^3$ are each a methyl group.

2.73 G. (0.01 mole) of quinoline yellow were dissolved in 35 ml. of dry methylene chloride. To the resultant solution was added by means of a syringe a solution of 6.54 g. (0.03 mole) of di-t-butyl dicarbonate in 10 ml. of methylene chloride, followed by 0.79 g. (0.80 ml., 0.01 mole) of pyridine. The resultant mixed was stirred overnight at ambient temperature. At this time, analysis of the reaction mixture by thin layer chromatography, using methylene chloride as the eluant, showed the presence of a heat-sensitive leuco dye, with substantial amounts of the starting material.

Accordingly, the stirring was continued for a further 24 hours at room temperature, then the reaction mixture was filtered to remove the solid which had precipitated.

Chromatographic analysis in the same manner as before showed the solid to be essentially free from starting material, but with some starting material remaining in the mother liquid. The mother liquid was therefore poured onto a silica gel column, which was eluted first with 1% hexane in methylene chloride and then with methylene chloride to elute the desired product. The eluate was evaporated to yield 0.425 g. of an off-white solid, which was recrystallized from 10 ml. of hexane to obtain, after cooling the hexane solution on an ice-bath, 0.309 g. of a colorless solid, melting point 140°–141° C., which turned yellow on exposure to heat or strong acid. The proton nuclear magnetic resonance and mass spectra were consistent with the expected structure.

Figure 2:
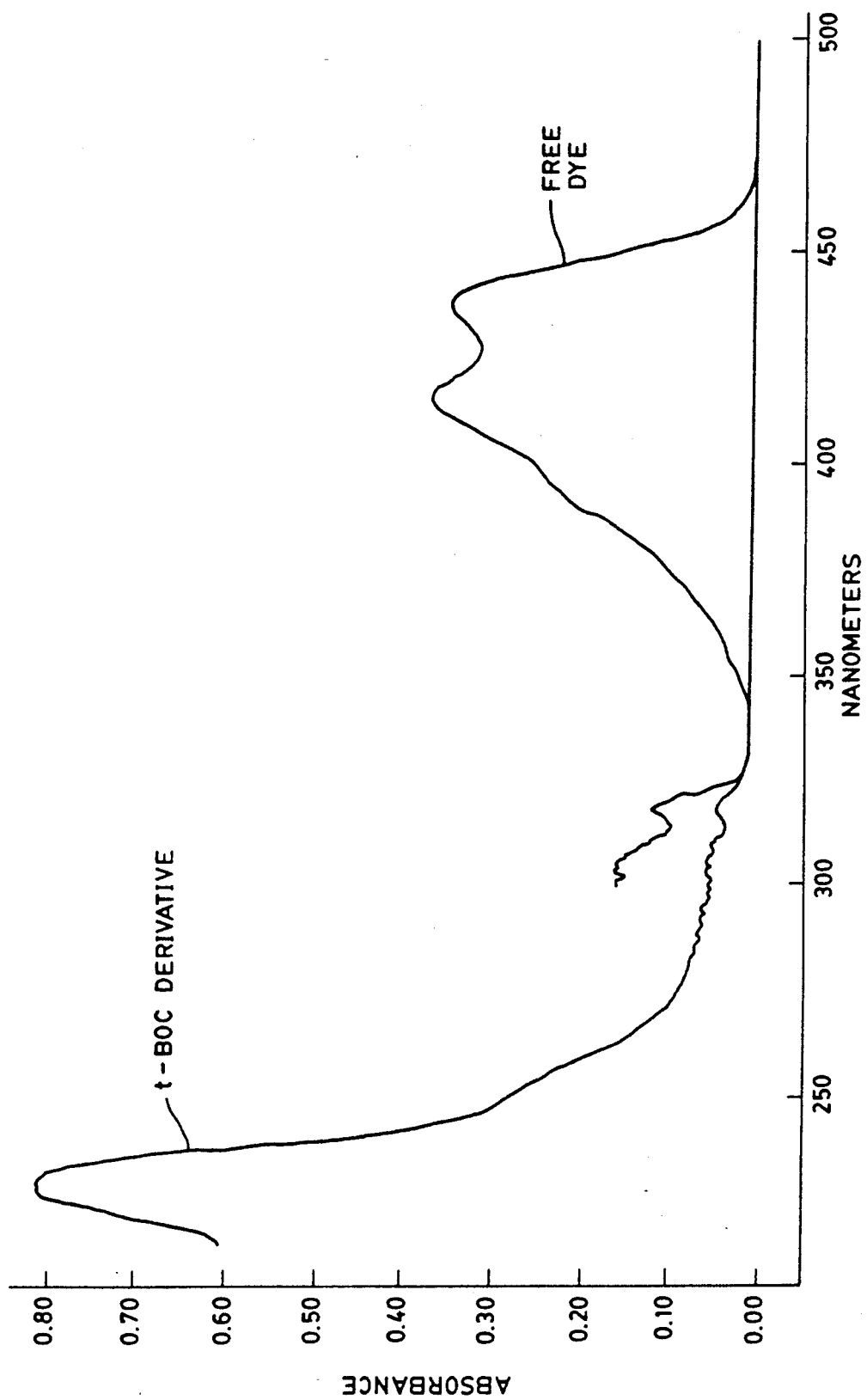
FIG. 2 shows the ultraviolet and visible spectra of quinoline yellow and its t-BOC derivative prepared in Example 1 below.

The ultraviolet/visible spectra of both the quinoline yellow starting material and the derivative are shown in FIG. 2 of the accompanying drawings. From FIG. 2, it will be seen that the derivative has a single absorption peak in the ultraviolet at 228 nm, with $\epsilon=66,300$; the derivative has essentially no absorption at wavelengths above about 326 nm., and hence appears colorless to the eye. On the other hand, the parent yellow dye, which is liberated by thermal decomposition of its derivative, has visible peaks at 415 nm. ($\epsilon=31,700$) and 438 nm. ($\epsilon=33,600$).

Example 2: Preparation of bis(t-BOC) derivative of terasil yellow

This Example illustrates the preparation of the bis(t-BOC) derivative of terasil yellow, the compound of Formula I in which R is an —O—C(=O)—O—C(CH$_3$)$_3$ group; X is a carbonyl group; R$^4$ is a hydrogen atom; and R$^1$, R$^2$ and R$^3$ are each a methyl group.

In the same way as in Example 1, a reaction mixture was formed comprising 15 g. (0.052 moles) of terasil yellow, 38.5 g. (0.1764 mole) of di-t-butyl dicarbonate, 8.2 g. (0.1037 mole) of pyridine and 350 ml. of dry methylene chloride. This reaction mixture was refluxed for 36 hours, and then analyzed by thin layer chromatography as described in Example 1 above. This analysis showed some remaining terasil yellow starting material. Accordingly, a further 3.5 g. of di-t-butyl dicarbonate was added, and the resultant mixture refluxed for a further 2 hours, after which time most of the yellow starting material had disappeared.

The reaction mixture was then filtered to remove a dark brown precipitate, and the methylene chloride was distilled off the filtrate, and ethanol added thereto, after which the mixture was allowed to sit in a refrigerator overnight; a brown precipitate (the first crop of crystals of the product) was formed and filtered off. Both the precipitate and the filtrate were analyzed by thin layer chromatography. Since it was found that the filtrate still contained a significant amount of the desired product, this filtrate was concentrated, then cooled and left overnight in the refrigerator. The second crop of crystals thus formed was separated by filtration, and the two crops of crystals combined to give 9.2 g. of a brown solid. This solid was dissolved in methylene chloride and the resultant solution treated with silica/celite to remove yellow-brown impurities (which had a lower R$_f$ than the product in the chromatographic analysis). The solvent was then evaporated off to produce 9.0 g. of a yellow product, which was subjected to a second silica/celite treatment in the same manner to give 8.35 g. (32% yield) of the desired colorless product. The proton nuclear magnetic resonance and mass spectra were consistent with the expected structure.

Figure 3:
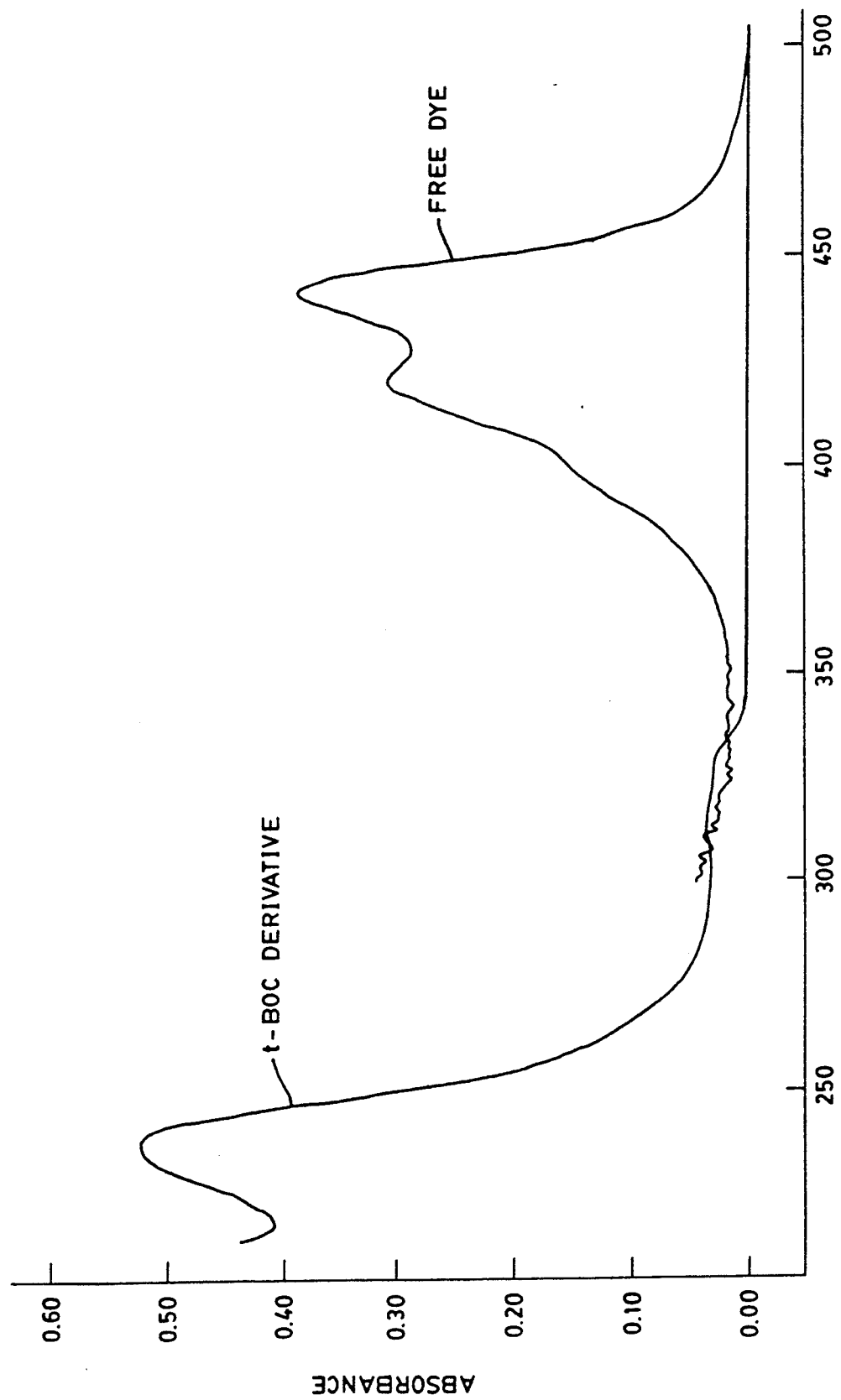
FIG. 3 shows the ultraviolet and visible spectra of terasil yellow and its bis(t-BOC) derivative prepared in Example 2 below.

The ultraviolet/visible spectra of both the terasil yellow starting material and the derivative are shown in FIG. 3 of the accompanying drawings. From FIG. 3, it will be seen that the derivative has a single strong absorption peak in the ultraviolet at 232 nm, with $\epsilon=17,000$; the derivative has essentially no absorption at wavelengths above about 350 nm., and hence appears colorless to the eye. On the other hand, the parent yellow dye, which is liberated by thermal decomposition of its derivative, has visible peaks at 420 nm. ($\epsilon=34,500$) and 442 nm. ($\epsilon=43,000$), and has essentially no absorption at wavelengths below about 340 nm.

Example 3: Preparation of t-BOC derivative of 3-Hydroxy-2,2'-quinolylthionaphthen This Example illustrates the preparation of the t-BOC derivative of 3-hydroxy-2,2'-quinolylthionaphthen, the compound of Formula I in which R and R$^4$ are each a hydrogen atom; X is a sulfur atom; and R$^1$, R$^2$ and R$^3$ are each a methyl group. The synthetic route used is shown in FIG. 1 of the accompanying drawings.

A. Preparation of 2,2'-dithiobenzoyl chloride

The following procedure is based upon J. Am. Chem. Soc., 68, 1831–37 (1946).

30.6 G. (0.1 mole) of dithiobenzoic acid were dissolved/suspended in 400 ml. of chloroform, and to this mixture were added successively 60.0 g. (0.5 mole) of thionyl chloride and 10 drops of dimethylformamide. The resultant mixture was refluxed for 6 hours to obtain a clear, tan reaction mixture, which was then stirred overnight at room temperature.

After this stirring, the solvent and excess thionyl chloride were removed under reduced pressure to yield an off-white solid, which was flushed twice with hexane to give an off-white solid, m. pt. 149°–152° C.

B. Preparation of m-chlorosulfylbenzoyl chloride

The product from Part A above was dissolved/suspended in 250–300 ml. of carbon tetrachloride and chlorine gas was bubbled through the mixture for approximately 30 minutes. The clear solution was decanted from the solids and excess chlorine and some solvent removed under reduced pressure. Fresh carbon tetrachloride was then added to the solution, which was left to stand in a refrigerator overnight. More solvent was removed under reduced pressure and replaced with fresh carbon tetrachloride to produce a solution, which was used directly in the next stage of the synthesis.

C. Preparation of benzenesulfonylbenzisothiazolone 31.44 G. (0.2 mole) of benzenesulfonamide was dissolved in 80 ml. of dry pyridine to obtain a clear, straw-colored solution, which was placed in a cold water bath. To this pyridine solution was added the carbon tetrachloride solution produced in Part B above. An exothermic reaction ensued with formation of a white slurry, which was stirred at ambient temperature for 45 minutes and then poured into 600 ml. of 2N hydrochloric acid. The aqueous phase of the resultant mixture was decanted from the lower organic phase, which was cooled in ice water and filtered to remove carbon tetrachloride. The white solid thus obtained was slurried in 600 ml. of hot acetic acid, cooled and filtered to obtain a white solid, which was dried under vacuum to yield 49.7 g. of product having an infra-red spectrum consistent with the expected structure. The ultraviolet spectrum of the product in methanol showed peaks at 202 nm ($\epsilon = 17,000$), 232 nm. ($\epsilon = 31,000$) and 332 nm. ($\epsilon = 4,000$).

D. Preparation of 3-hydroxy-2,2'-quinolylthionaphthen 12.0 G. (0.041 mole) of benzenesulfonylbenzisothiazolone was dissolved/suspended in 100 ml. of chloroform and to the resultant mixture were added successively 12.0 g. of quinaldine and 8 drops of N,N-diisopropylethylamine. The mixture was then refluxed for 4 hours, cooled to ambient temperature and stirred at ambient temperature for about 60 hours.

The solvent was distilled off from the resultant red-yellow reaction mixture to leave a red mass, which was diluted with hexane and filtered to yield 17.4 g. of a red crystalline solid. This solid was recrystallized from 130 ml. of toluene and extracted with three separate portions of boiling water to leave behind a red solid, which was dried under vacuum. The final yield was 7.9 g. (78.2%) of solid, m. pt. 183°-186° C. The mass and infra-red spectra were consistent with the expected structure.

E. Preparation of t-BOC derivative of 3-Hydroxy-2,2'-quinolylthionaphthen 2.7 G. (0.01 mole) of the 3-hydroxy-2,2'-quinolylthionaphthen prepared in Part D above were dissolved/suspended in 35 ml. of methylene chloride, and to this mixture were added 6.54 g. (0.03 mole) of di-tert-butyl dicarbonate and 0.80 g. of pyridine. The resultant mixture was refluxed for 1 hour; during this time, the orange-red liquid became colorless. After the refluxing, the solvent was removed under reduced pressure to obtain a colorless oil, to which was added a small amount of hexane. The mixture was cooled in an ice-water bath to produce separation of a white solid, which was washed with cold hexane and dried in air at ambient temperature. The yield was 2.7 g. of the white solid, m. pt. 126°-128° C. A spot of this solid on a plate gave a orange spot upon heating. The infra-red spectrum was consistent with the expected structure.

Figure 4:
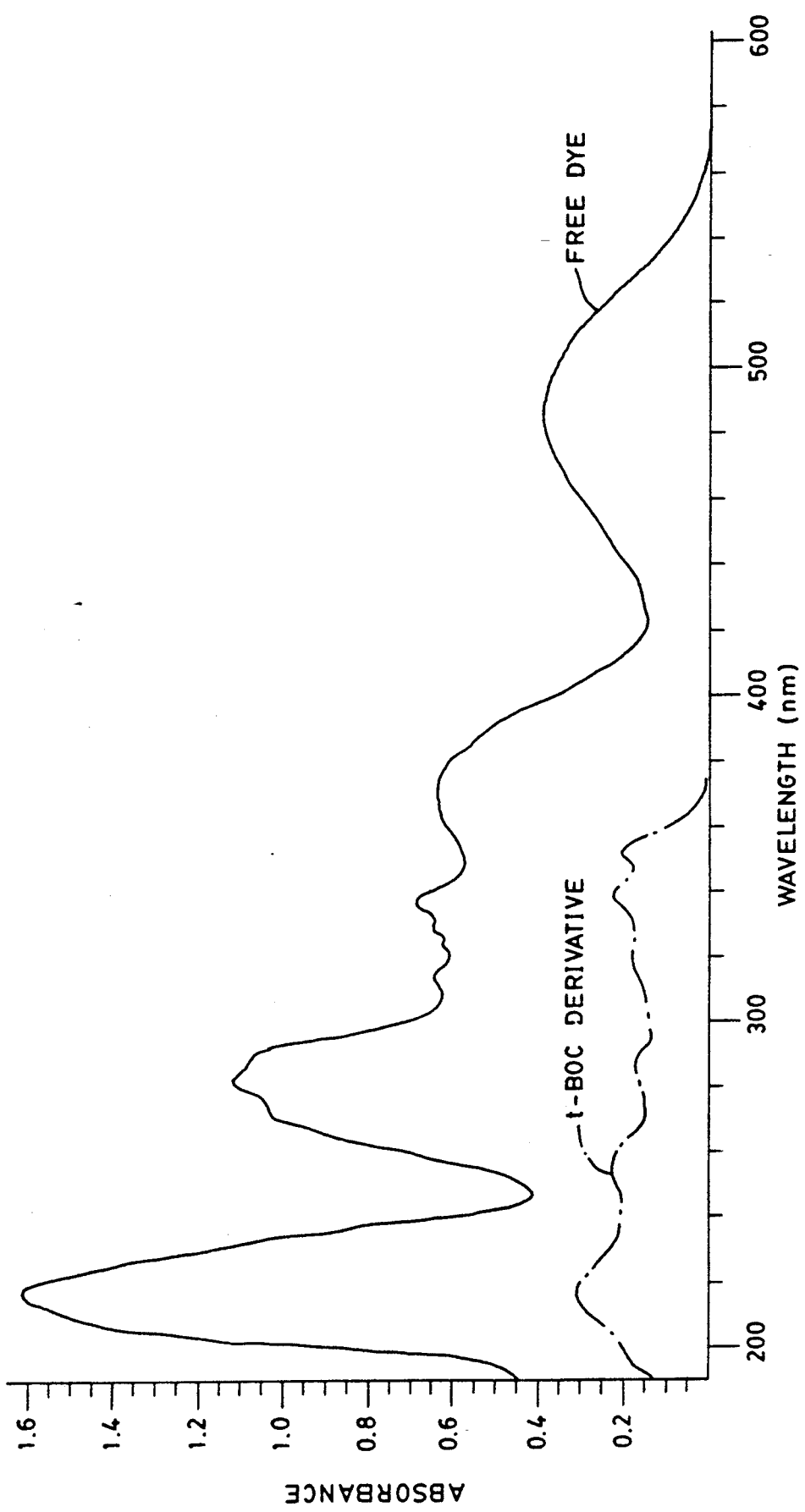
FIG. 4 shows the ultraviolet and visible spectra of the t-BOC derivative of the dye shown in FIG. 1 and the free dye itself, as prepared in Example 3 below.

The ultraviolet/visible spectra of both the parent dye produced in Part D above and the t-BOC derivative are shown in FIG. 4 of the accompanying drawings. From FIG. 4, it will be seen that the derivative has absorption peaks in the ultraviolet at 216 nm. ($\epsilon = 32,000$), 240 nm. (68 = 22,100), 260 nm. ($\epsilon = 23,700$), 286 nm. ($\epsilon = 18,800$), 320 nm. ($\epsilon = 19,100$), 338 nm. ($\epsilon = 24,000$) and 352 nm. ($\epsilon = 22,100$); the derivative has essentially no absorption at wavelengths above about 375 nm., and hence appears colorless to the eye. On the other hand, the parent dye, which is liberated by thermal decomposition of its derivative, has peaks at 282 nm. ($\epsilon = 22,800$), 314 nm. ($\epsilon = 13,100$), 338 nm. ($\epsilon = 13,900$), 370 nm. ($\epsilon = 13,100$) and 486 nm ($\epsilon = 7,800$).

Example 4: preparation of heat-sensitive element

This Example illustrates the preparation of a heat-sensitive element of the present invention comprising the bis(t-BOC) derivative of terasil yellow prepared in Example 2 above.

A coating composition was prepared by mixing 28 ml. of methyl ethyl ketone, 2 ml. of methylene chloride, 1.4 g. of polyethyl oxazoline, 1.2 g. of the bis(t-BOC) derivative of terasil yellow prepared in Example 2 above, and 0.04 g. of an infra-red absorber of the formula:

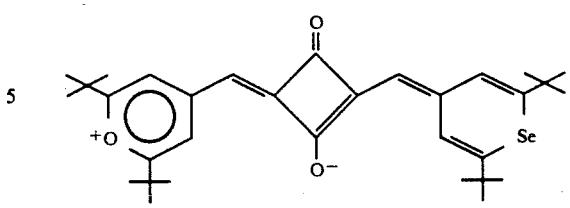

This coating composition was coated onto a polyester film approximately 4 mil thick at a coating weight sufficient to produce a layer of the coating composition approximately 1 µm thick. The resultant heat-sensitive was imaged by passing across it a beam from a laser scanner at a wavelength of 825 nm. at speeds of 0.25, 0.50 and 0.75 m/sec. The heat-sensitive element developed intense yellow bands at scanning speeds of 0.25 and 0.50 m/sec.

Example 5: Preparation of heat-sensitive element

This Example illustrates the preparation of a second heat-sensitive element of the present invention comprising the bis(t-BOC) derivative of terasil yellow prepared in Example 2 above.

Example 4 was repeated, except that the infra-red absorber used was of the formula:

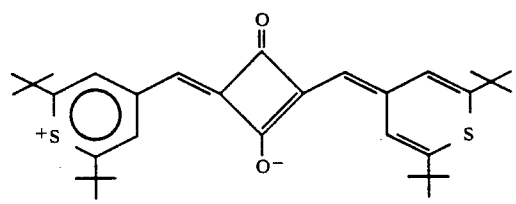

The composition was coated and imaged in the same manner as in Example 4, using a scanning speed of 0.5 m/sec. The heat-sensitive element developed intense yellow bands in the imaged regions.

We claim:

1. A process for the preparation of a mixed ester of carbonic acid and:
   a) a quinophthalone dye; and
   b) a teriary alkanol containing not more than about 9 carbon atoms, which process comprises reacting a quinophthalone dye with the corresponding di-tertiary alkyl dicarbonate in the presence of a base.

2. A process according to claim 1 wherein the mixed ester produced is an ester of a teriary alkanol containing not more than about 6 carbon atoms.

3. An ester of the formula:

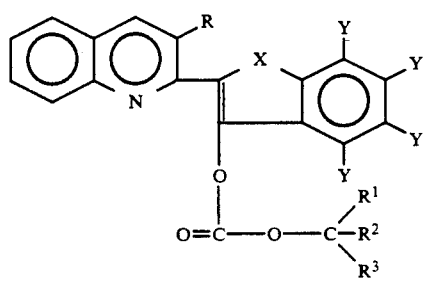

wherein X is a sulfur atom or a carbonyl group; each Y independently is a hydrogen atom, a halogen atom, a —CO—OR⁴ or a —CO—NHR⁴ group, where R⁴ is an alkyl group containing not more than about 10 carbon atoms; R is a hydrogen atom or an —O—C(=O)—O—CR⁵R⁶R⁷ group; and R¹, R², R³, R⁵, R⁶ and R⁷ are each an alkyl group, subject to the proviso that R¹, R² and R³ together contain a total of not more than about 8 carbon atoms, and R⁵, R⁶ and R⁷ together contain a total of not more than about 8 carbon atoms.

4. An ester according to claim 3 wherein X is a carbonyl group.

5. An ester according to claim 3 wherein each Y is a hydrogen atom.

6. An ester according to claim 3 wherein R¹, R² and R³ together contain not more than about 5 carbon atoms.

7. An ester according to claim 6 wherein R¹, R² and R³ are each a methyl group.

8. An ester according to claim 3 wherein R⁵, R⁶ and R⁷ together contain not more than about 5 carbon atoms.

9. An ester according to claim 8 wherein R⁵, R⁶ and R⁷ are each a methyl group.

10. The ester according to claim 3 wherein R is a hydrogen atom; X is a carbonyl group; each Y is a hydrogen atom; and R¹, R² and R³ are each a methyl group.

11. The ester according to claim 3 wherein R is an —O—C(=O)—O—C(CH₃)₃ group; X is a carbonyl group; each Y is a hydrogen atom; and R¹, R² and R³ are each a methyl group.

12. A process according to claim 1, wherein the quinophthalone dye is of the formula:

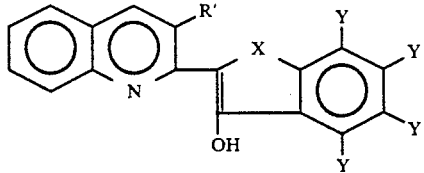

wherein R' is a hydrogen atom or a hydroxyl group; each Y independently is a hydrogen atom, a halogen atom, a —CO—OR⁴ or a —CO—NHR⁴ group, where R⁴ is an alkyl group containing not more than about 10 carbon atoms; and X is a sulfur atom or a carbonyl group.

13. A process according to claim 12 wherein the starting materials are quinoline yellow and di-tertiary butyl carbonate and the product is the ester claimed in claim 10.

14. A process according to claim 12 wherein the starting materials are terasil yellow and di-tertiary butyl carbonate and the product is the ester claimed in claim 11.

15. A mixed ester of carbonic acid and:
a) a quniophthalone dye; and
b) a tertiary alkanol containing not more than about 9 carbon atoms, which ester has been produced by a processing according to claim 1.

16. A mixed ester of carbonic acid and:
a) a quinophthalone dye; and
b) a tertiary alkanol containing not more than about 6 carbon atoms, which ester has been produced by a process according to claim 2.

* * * * *